United States Patent [19]

Laborit et al.

[11] Patent Number: 4,906,620
[45] Date of Patent: Mar. 6, 1990

[54] MEDICAMENT COMPRISING AS ACTIVE INGREDIENT N⁶ SUBSTITUTED ADENOSINE

[75] Inventors: Henri Laborit, Paris; Camille George Wemuth, Illkiren, both of France

[73] Assignee: Centre d'Etudes Experimentales et Cliniques de Physio-Biologie de Pharmacologie et d'Eutonologie (CEPBEPE) and Centre National de la Recherche Scientifique, France

[21] Appl. No.: 297,558

[22] Filed: Jan. 13, 1989

Related U.S. Application Data

[63] Continuation of Ser. No. 807,817, Dec. 11, 1985, abandoned.

[30] Foreign Application Priority Data

Dec. 13, 1984 [FR] France ................. 84 19047

[51] Int. Cl.⁴ .................. A61K 31/70; C07H 19/167
[52] U.S. Cl. ........................ 514/46; 514/45; 536/23; 536/24; 536/26
[58] Field of Search ............. 536/24, 26; 514/45, 514/46

[56] References Cited

U.S. PATENT DOCUMENTS

| | | | |
|---|---|---|---|
| 4,171,432 | 10/1979 | Carrico et al. | 536/26 |
| 4,282,352 | 8/1981 | Imahori et al. | 536/27 |
| 4,340,730 | 6/1982 | Henderson et al. | 536/26 |
| 4,388,308 | 6/1983 | Hamilton et al. | 424/180 |
| 4,616,003 | 10/1986 | Hamilton et al. | 514/46 |
| 4,626,526 | 12/1986 | Bristol | 514/46 |

FOREIGN PATENT DOCUMENTS

| | | | |
|---|---|---|---|
| 9030395 | 3/1974 | Japan | 536/24 |
| 9030397 | 3/1974 | Japan | 536/24 |
| 9030396 | 8/1974 | Japan | 536/24 |
| 2077725 | 12/1981 | United Kingdom | 536/26 |

OTHER PUBLICATIONS

Letham et al., Chemical Abstracts, vol. 91; 16735h (1979).
Kikugawa et al., J. Medicinal Chemistry, vol. 16, 358–364(1973).

*Primary Examiner*—Johnnie R. Brown
*Assistant Examiner*—L. Eric Crane
*Attorney, Agent, or Firm*—Jacobs & Jacobs

[57] ABSTRACT

New Medicament comprising as active ingredient a N⁶-substituted adenosine of formula I

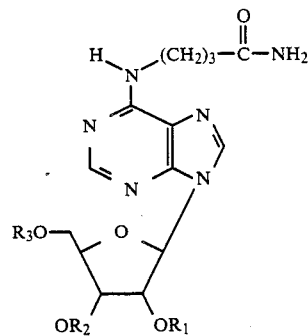

wherein $R_1$, $R_2$ and $R_3$ are each independently hydrogen or acyl $R_4$-CO- in which $R_4$ is alkyl, aryl, heteroaryl or aralkyl.

11 Claims, No Drawings

MEDICAMENT COMPRISING AS ACTIVE INGREDIENT N⁶ SUBSTITUTED ADENOSINE

This is a continuation of Ser. No. 807,817 filed Dec. 11, 1985, now abandoned.

BACKGROUND OF THE INVENTION

The present invention relates to a new medicament, comprising as active ingredient $N^6$ substituted adenosine, of formula I

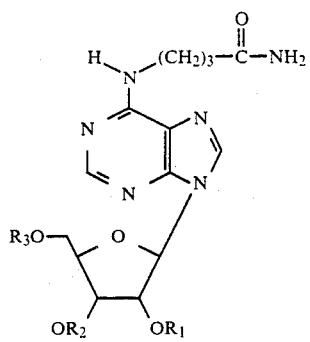

in which $R_1$, $R_2$ and $R_3$ are each independently hydrogen or acyl $R_4$—CO— wherein $R_4$ is alkyl, aryl, heteroaryl or aralkyl.

SUMMARY OF THE INVENTION $N^6$ substituted adenosines are already known by U.S. No. 4,340,730 for the general treatment of hypertension, but the new medicament is distinguished therefrom by the extent of its field of activity, the power and duration of its actions.

The method of synthesizing the hydrochlorate of the new compound, designated hereafter Agr 529, will now be described.

A mixture of 4 g (13.2 mmoles) of chloro-6 purine riboside, 3.6 g (26.4 mmoles) of amide γ-amino butyric hydrochlorate and 4 g (39.6 mmoles) of triethylamine are heated at reflux for ten hours in 50 ml of an ethanol-water mixture (8:2).

The solution is left to cool, which causes the formation of a precipitate which is filtered. This precipitate is recrystallized a first time in water, then in absolute ethanol. 3.5 g of a white flocculent precipitate is obtained, i.e. 9.9 mmoles (75%) C.C.M.: Rf=0.66

| Cellulose F plaque | 0.1 mm |
|---|---|
| Migration solvent $NH_3$ | 10% |
| $H_2O$ | 20% |
| Isopropanol | 70% |

Melding point: 215° C.

These 9.9. mmoles of $N_6$-(carboxamido-3 propyl) adenosine are dissolved in 400 ml of hot isopropanol to which 10 mmoles of concentrated 35% HCL, i.e. 0.36 g, are added drop by drop. It is left to cool and the expected hydrochlorate precipitates. The precipitate is filtered which gives 3 g (78%) of white powder. Melting point: 170° C. Analysis:

| calculated: | C: 43.5; | H: 5.45; | N: 21.67 |
|---|---|---|---|
| found: | C: 43.20; | H: 5.60; | N: 21.30 |

RMN spectrum: confirms the structure of the product.

A complete pharmacological evaluation is given of the basis medicament, called thereafter Agr 529, comprising an active ingredient—the compound of formula I, wherein, $R_1$, $R_2$ and $R_3$ each are hydrogen.

The toxicity of Agr 529 was tested on rats, using 7 male rats of 250–300 grams, the Agr 529 being administered intraperitoneally. The result of the test is given in the table below, given the percentage of mortality as a function of time.

| | TOXICITY OF AGR 529 ON RATS | | | | |
|---|---|---|---|---|---|
| Doses of Agr 529 | % Mortality at 1 hour | % Mortality at 2 hours | % Mortality at 6 hours | % Mortality at 24 hours | % Mortality at 7 days |
| 500 mg/kg | 0% | 0% | 0% | 100% | / |
| 350 mg/kg | 0% | 0% | 0% | 100% | / |
| 300 mg/kg | 0% | 0% | 0% | 0% | 100% (48 h) |
| 250 mg/kg | 0% | 0% | 0% | 0% | 0% |

It can be seen that for doses less than or equal to 250 mg/kg the mortality is zero at 7 days and more.

The pharmacological doses are situated between 0.25 and 50 mg/kg.

ANTI-INFLAMMATORY ACTION

This action was tested on the oedema caused by kaolin in male rats, Spraque-Dawley, of an average weight of 350 g. The animals were divided at random into four groups, a reference group which received intraperitoneally (ip) physiological serum, and three treated groups called TESTS 1, TESTS 2, TESTS 3 which received (ip) Agr 529, respectively 5 mg/kg, 10 mg/kg and 50 mg/kg. Then thirty minutes after the treatment all the animals received under the plantar 0.1 ml of a 10% kaolin suspension. The volume of the paw was measured by means of a plethysometer (Hugo Basile 7150) one hour before the oedema and one, two, four and five hours afterwards.

The results given in Table 1, (see page 4) show that at the dose of 50 mg/kg, the Agr 529 provides 100% inhibition at the fourth hour and has an anti-inflammatory action which is already considerable for 5 and 10 mg/kg.

ANALGESIC ACTION

This action was tested on male mice of 30 grams, the Agr 529 being administered intraperitoneally and the test used being that of the heating plate.

The apparatus used was an analgesimeter with electric heating plate SOCREL (Apelex). The temperature of the plate was stabilized at 56° C. The response time was noted corresponding to the time required by the animal for licking its front or rear paws. For each animal, the average response time corresponds to the average of three consecutive measurements. The test was carried out at time 0 then 10 minutes after the injection of the drug then 30 minutes afterwards.

The result are give in tables 2 below and 3 (v. pages 5, 6) which show the important analgesic action of the molecule.

TABLE 1

Evolution of the volume of the paw expressed as a percentage of the initial volume.

| | Treatment | Oedema t = 0 | 1 hour | 2 hours | 4 hours | 5 hours |
|---|---|---|---|---|---|---|
| References | Isotonic aqueous salt solution 9% | Kaolin | 15.3 ± 2.25 | 17.35 ± 2.4 | 20.9 ± 2.8 (6) | 21.1 ± 5.7 |
| TESTS 1 | Agr 529 5 mg/kg | Kaolin | 8.1 ± 2.3 | 11.0 ± 3.3 | 9.6 ± 3.3 (5) | 12.8 ± 1.6 |
| TESTS 2 | Agr 529 10 mg/kg | Kaolin | 10.1 ± 1.3 | 9.9 ± 1.3 | 8.4 ± 1.1 (5) | 7.1 ± 1.55 |
| TESTS 3 | Agr 529 50 mg/kg | Kaolin | 1.3 ± 2.4 | −0.15 ± 3.0 | 1.3 ± 2.3 | — |

TABLE 2

| ANALGESIC TEST | Nature & Doses of the product tested. | Mean initial time of response to the test $t_o$ in seconds | Mean time of response to the test 10 min after injection of the product considered $t_{10}$ in secs. | Mean response time to the test 30 mins after injection of the product considered $t_{30}$ in secs. |
|---|---|---|---|---|
| Heating Plate 56° | Isotonic aqueous salt solution 9% iP | 4.2 ∓ 0.3 | 4.9 ∓ 0.4 | 4.9 ∓ 0.4 |
| Heating Plate 56° | AGR 529 10 mg/kg iP | 3.4 ∓ 0.5 | 18.4 ∓ 2.4 | 15.4 ∓ 4.9 |
| Heating Plate 56° | AGR 529 5 mg/kg iP | 3.3 ∓ 0.5 | 8.3 ∓ 11.5 | 9.2 ∓ 1.9 |

TABLE 3

Study of the analgesic effect consecutive to the intraperitoneal administration of Agr 529 at the dose of 1 mg/kg

| Analgesic Test | Nature & Dose of the product Tested | Mean initial time of response to the test in seconds t = 0 | Mean time of response to the test 10 mins after injection of the product in seconds t = 10 |
|---|---|---|---|
| Heating plate 56° C. | n = 8 Isontonic aqueous salt solution 9% i.p. | 6.1 ± 0.6 (2.5012) | +13% NS 6.9 ± 0.6 (2.4993) |
| Heating plate 56° C. | n = 8 Agr 529 1 mg/kg i.p. | 6.3 ± 0.7 (4.4479) | +81% S +65% 11.4 ± 1.9 (28.22) |

The comparison of the batches was made by the Student test with: NS: non significant: and *P < 0.05

THE ACTION ON LOCOMOTOR ACTIVITY

It was tested on mice using an electronic automatic counting device which records separately the displacements and straightening movements of two batches of five male mice, every five minutes and for an hour.

The evolution of the motor activity is compared with that of a reference batch in which the animals received isotonic aqueous salt solution under the same conditions as the batch subjected to the action of the Agr 529 intraperitoneally.

It was discovered that from a dose of 1 mg/kg the Agr 529 led to a reduction of 75% of activity after one hour.

The molecule of the invention has a highly hypotensive or anti-hypertensive action, as is proved more particularly by the fact that, injected by intravenous perfusion in rats of 25 to 50 mg/kg, the Agr 529 caused a drop of tension of 40 mm of Hg. Intraperitoneally, a dose of 10 mg/kg, it potentializes the drop of tension due to phenobarbital injected intraperitoneally in doses of 12 or 30 mg/kg.

The interest of Agr 529 in anaesthesia is demonstrated by the fact that in rats, for a dose of pentobarbital (PB) inducing anaesthesic sleep (30 mg/kg, i.p.), the administration 30 minutes before of 10 mg/kg of Agr 529 increases the duration of the narcosis by 119%.

For an i.p. dose of PB of 12 mg/kg, which does not cause the animal to lose its recovery reflex, the injection (i.p.) thirty minutes before of 10 mg/kg of Agr 529 causes a narcosis comparable to that of the anaesthetic doses of PB (30 mg/kg).

From the pharmacological study a large number of pathological disorders may therefore be proposed as therapeutic indications for use of the molecule of the invention.

The anti-inflammatory, analgesic, tranquilizing, antihypertensive an anaesthesic effects have been more particularly mentioned.

As mentioned above, the compound of the invention is distinguished from known $N^6$ substituted adenosines more especially by the power of its action.

Thus it is that if we compare the action on the locomotor activity of Agr 529 and of the compound of formula (X)

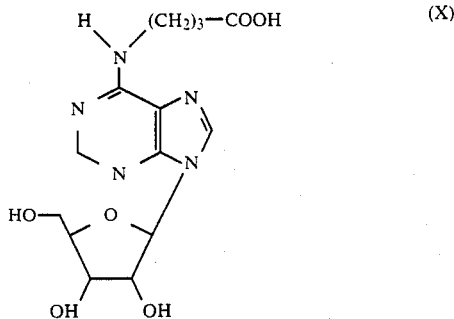

it can be seen that in order to obtain a reduction, after one hour, of the locomotor activity of 75%, an i.p. injection must be used of 14 mg/kg of compound X
and 1 mg/kg of Agr 529, which in this test seems therefore 14 times more powerful.

Similarly, the analgesic action of Agr 529 of compound X and another known $N^6$ substituted adenosine of formula Y was compared (by the heating plate test)

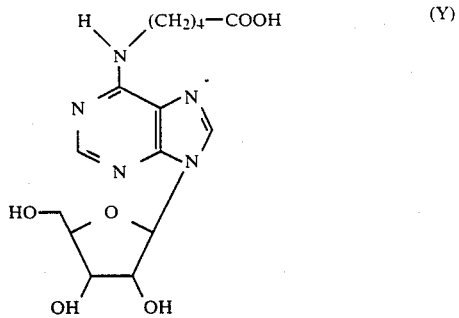

The results of the comparative test are given in the following table where the percentages of increase in the response time are given 10 minutes and 30 minutes after injection of the drug, with respect to the response time at time 0.

|  | 10 Minutes | 30 Minutes |
| --- | --- | --- |
| X (70 mg/kg) | +306.25% | +342.85% |
| Y (73 mg/kg) | +135% | +230% |
| Agr 529 (10 mg/kg) | +440% | +353% |

It can be seen that Agr 529 has a considerably higher analgesic action than that of compounds X and Y and in particular than that of compound Y.

Besides the intraperitoneal form of administration, the use of intravenous, intramuscular and oral methods will be proposed clinically.

The intravenous doses in rabbits extends between 1 and 75 mg.kg with definitive survival. For testing on human beings, doses of 0.5 to 10 mg/kg may be considered for intravenous introduction.

For intramuscular introduction in human beings, an intermediate dose may be considered to be useful.

Orally (intubation) in animals, doses ten times greater than the doses used intraperitoneally are required. It may be considered that in human beings doses of 50 mg/kg will be useful.

For oral administration, it is preferable to use the compounds of formula I wherein $R_1$ and/or $R_2$ and/or $R_3$ are aryl $R_4$—Co, $R_4$ being alkyl, aryl etheraly or aralkyl.

There are thus obtained, starting from medicament Agr 529, lipophile esters of the primary alcohol functions which are, what are called "prodrugs" which gives to the Agr 529 a good activity by oral administration.

As an example of such "prodrugs" is cited the product having as active ingredient the compound of formula I wherein $R_1$, $R_2$ and $R_3$ each are $CH_3$—$CH_2$—CO—, i.e. (Carboxamido-3 propyl)-6, (tripropionyl)-$2',3',5'$, $\beta$, D ribosyl)-9 purine of structural formula: $C_{23}H_{32}N_6O_8$.

The above compound is obtained by reacting with the active ingredient of Agr 529, pyridine together with propionic anhydride.

Preparation of (Carboxamido-3 propylamino)-6, (tripropionyl $2'$, $3'$, $5'$ $\beta$, D ribosyl)-9 purine.

In a flask of 100 ml, are introduced 25 ml of pyridine and 25 ml of propionic anhydride. 1 g of $N_6$-(carboxamido-3-propyl)adenosine are added and heated with magnetic stirring to 80° C. This temperature is maintained until complete dissolving of the $N_6$-(carboxamido-3-propyl)adenosine. The mixture is then dry evaporated. The resultant oil is purified by elution chromatography on silica (solvent=dichloromethane-methanol: 90-10). With chromatography on thin film, a pale yellow oil is obtained.

What is claimed is:

1. A compound of the formula

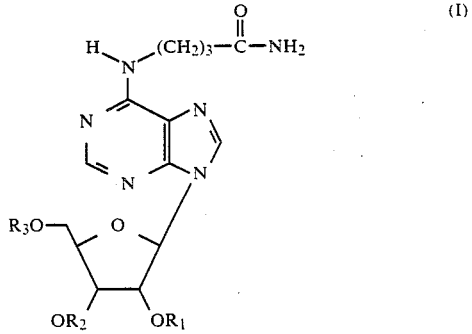

wherein $R_1$, $R_2$, and $R_3$ are the same or different and each is hydrogen or $R_4$—CO— wherein $R_4$ is alkyl, aryl, heteroaryl, or aralkyl.

2. A compound according to claim 1 wherein $R_1$, $R_2$, and $R_3$ are each hydrogen.

3. A compound according to claim 1 wherein $R_1$, $R_2$, and $R_3$ are each $CH_3$—$CH_2$—CO—.

4. A lipophilic carboxylic acid ester prodrug of one or more of the hydroxyl groups of the compound of the formula 5. A prodrug according to claim 4 wherein the prodrug ester is $CH_3-CH_2-CO-$.

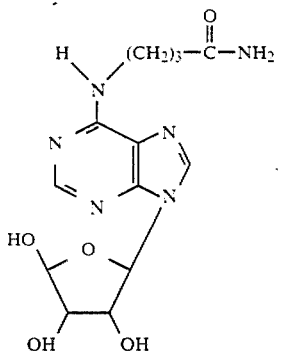

6. A pharmaceutical composition useful for effecting anti-inflammatory, analgesic, tranquilizing, and antihypertensive effects in humans and animals which comprises a therapeutically effective amount of a compound of the formula

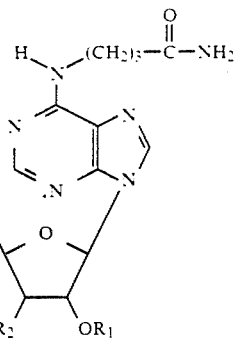

wherein $R_1$, $R_2$ and $R_3$ are the same or different and each is hydrogen or $R_4-CO-$ wherein $R_4$ is alkyl, aryl, heteroaryl or aralkyl, in combination with a pharmaceutically acceptable carrier.

7. A composition according to claim 6 wherein $R_1$, $R_2$ and $R_3$ are each hydrogen.

8. A composition according to claim 6 wherein $R_1$, $R_2$ and $R_3$ are each $CH_3-CH_2-CO-$.

9. A method for treating inflammation, pain, and hypertension, and providing a tranquilizing effect, in humans and animals which comprises administering to a human or animal in need thereof a therapeutically effective amount of a compound of the formula

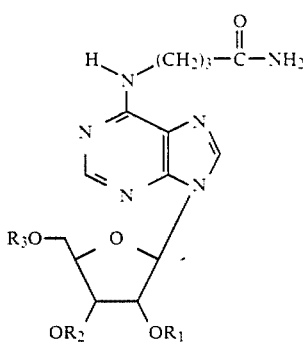

wherein $R_1$, $R_2$ and $R_3$ are the same or different and each is hydrogen or $R_4-CO-$ wherein $R_4$ is alkyl, aryl, heteroaryl or aralkyl, in combination with a pharmaceutically acceptable carrier.

10. A method according to claim 9 wherein $R_1$, $R_2$ and $R_3$ are each hydrogen.

11. A method according to claim 9 wherein $R_1$, $R_2$ and $R_3$ are each $CH_3-CH_2-CO-$.

* * * * *